United States Patent
Todd (10) Patent No.: US 10,823,722 B2
(45) Date of Patent: Nov. 3, 2020

(54) PROBE FOR MEASURING THE BIOMASS CONTENT IN A MEDIUM

(71) Applicant: Aber Instruments Limited, Aberystwyth (GB)

(72) Inventor: Robert Todd, Aberystwyth Dyfed (GB)

(73) Assignee: Aber Instruments Limited, Aberystwyth (GB)

( * ) Notice: Subject to any disclaimer, the term of this patent is extended or adjusted under 35 U.S.C. 154(b) by 411 days.

(21) Appl. No.: 15/533,796

(22) PCT Filed: Dec. 7, 2015

(86) PCT No.: PCT/GB2015/053741
§ 371 (c)(1),
(2) Date: Jun. 7, 2017

(87) PCT Pub. No.: WO2016/092281
PCT Pub. Date: Jun. 16, 2016

(65) Prior Publication Data
US 2017/0328880 A1    Nov. 16, 2017

(30) Foreign Application Priority Data
Dec. 12, 2014  (GB) .................................. 1422119.6

(51) Int. Cl.
*G01N 33/487* (2006.01)
*G01N 27/22* (2006.01)
(Continued)

(52) U.S. Cl.
CPC ....... *G01N 33/48735* (2013.01); *G01N 27/07* (2013.01); *G01N 27/226* (2013.01); *C12M 41/36* (2013.01)

(58) Field of Classification Search
CPC ..................... G01N 33/48735; C12M 41/36
See application file for complete search history.

(56) References Cited

U.S. PATENT DOCUMENTS

2003/0070942 A1    4/2003    Ossart

FOREIGN PATENT DOCUMENTS

| EP | 2 405 263 A2 | 1/2012 |
| EP | 2 725 095 A1 | 4/2014 |

OTHER PUBLICATIONS

United Kingdom Office Action, dated Jun. 29, 2015, application P508788.

*Primary Examiner* — Jonathan M Hurst
(74) *Attorney, Agent, or Firm* — Muskin and Farmer LLC (57) ABSTRACT

The invention relates to a probe for measuring the biomass content in a medium having a suspending fluid and cells. The probe has at least three electrodes, wherein two of the electrodes are configured as excitation electrodes for transmitting an excitation signal through a medium. Two of the electrodes are configured as signal electrodes for receiving an excitation signal that has passed through the medium. The or each signal electrode is located between the two excitation electrodes at a position where a high current density is generated. The probe can have two excitation electrodes and four signal electrodes. The signal electrodes are configured substantially in parallel and arranged in couples adjacent each other, at positions between the excitation electrodes. The signal electrodes are configured such that (i) a first couple of signal electrodes are arranged between the closest end points of the excitation electrodes at one side of the probe, and (ii) a second couple of signal electrodes are arranged between the closest end points of the excitation electrodes at the other side of the probe.

21 Claims, 4 Drawing Sheets

(51) Int. Cl.
*G01N 27/07* (2006.01)
*C12M 1/34* (2006.01)

PROBE FOR MEASURING THE BIOMASS CONTENT IN A MEDIUM

The invention relates to a probe for measuring the biomass content of a medium. The invention also relates to an apparatus incorporating said probe, and a system having said apparatus or probe.

The fermentation industry requires equipment that can measure the biomass content of a medium for a very broad range of cell types using a very wide range of culturing conditional. Regulatory requirements demand accurate analysis and process control.

Known biomass measurement techniques involve introducing metal electrodes into the liquid and applying an excitation signal and measuring voltage and current using measurement electrodes. The impedance, conductivity and specific capacitance can then be calculated. Unfortunately, at frequencies below around 1 MHz, and particularly where the conductivity is high (up to 100 mS/cm or so), the electrode-liquid interface exhibits an impedance which appears in series with the impedance of interest and distorts the measurements. These errors also vary with time as the electrode surface impedance is not stable and also depends upon electrode surface current density. Analysis equipment and methods are known from GB2329711 and GB2481832. Known methods provide means for establishing correction factors to deal with electrode polarisation errors.

Figure 1:
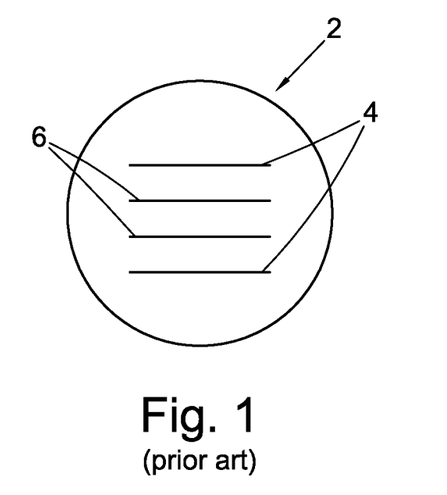

FIG. 1 shows a known component 2 having four electrodes in which two outer wires 4 are used to pass a current through a medium to be analysed, while the two inner wires 6 are used to detect the voltage drop across the suspension between the outer electrodes.

The inventor has realised that non-uniformity of the electrode fields and of electrode current density means that known methods and probe arrangements cannot avoid the polarisation effect entirely, particularly in highly conductive media.

It is an object of the present invention to address problems and limitations of known probes to provide an improved probe, apparatus and/or system for measuring the microbial content or other biomass in a culture for improving a fermentation process, preferably in real time and preferably in situ. From one aspect, the invention resides in a probe for measuring the biomass content in a medium having a suspending fluid and cells, the probe having at least three electrodes, wherein two of the electrodes are configured as excitation electrodes for transmitting an excitation signal through a medium, and said excitation electrodes are configured such that the current density of an excitation signal passing between said excitation electrodes through said medium varies along the length of the excitation electrodes, wherein two of the electrodes are configured as signal electrodes for measuring a voltage therebetween that has been generated by an excitation signal passing between the excitation electrodes, and where only three electrodes are provided the signal couple of electrodes comprise one of the excitation electrodes and a single sensing electrode, wherein one of the signal electrodes or each signal electrodes is located between the two excitation electrodes at a position where high or higher current density occurs such that the or each signal electrode is aligned with, or located on or adjacent, a current path which has substantially the same current phase as the total excitation current.

The inventor has realised that, on known probes, the phase of the voltage measured by the signal electrodes is actually an average or weighted average of the phases of the voltages measured along each current path that extend between the excitation electrodes. Therefore, the or each signal electrode of the invention can be configured and/or positioned to lie in a region where high or higher current density occurs to improve performance. The or each signal electrode can be aligned with the higher density current path.

One of the signal electrodes or each signal electrode, and the excitation electrodes, can be different lengths or shapes. The configuration or format of the probe can determine the length or shape of the excitation electrodes and/or signal electrodes. Changing the shape or length can influence the current path between the excitation electrodes.

The shape or length of an electrode can be configured to optimise performance of the probe by inhibiting the influence of the polarisation impedance, which is current dependent. By way of example, the polarisation impedance can vary along the excitation electrode's length.

The electrodes can lie on substantially the same plane. The excitation electrodes can be the substantially the same length. The excitation electrodes can be substantially parallel.

The or each signal electrode can be shorter that the excitation electrode. The length of the or each signal electrode can be less than around one third the length of an excitation electrode i.e. a ratio of 1:3. Said ratio can be less that 1:4 or can be less than 1:5. Preferably, said ratio is 1:6. An outer end of the or each signal electrode can be substantially aligned with the ends of the excitation electrodes.

The surface area of one of the excitation electrodes can be greater than the other excitation electrode. The conductive surface area of the excitation electrodes can be greater than the surface area of the or each signal electrode. The surface area of the excitation electrodes can be at least five times greater than the surface area of the or each signal electrode.

The or each signal electrode can be positioned around the region of a mid-point between the excitation electrodes, and preferably substantially half-way between the excitation electrodes. The or each signal electrode can be configured to be substantially parallel to the excitation electrodes. The electrodes can be symmetrically positioned around a centre region of the probe. This improves the ability of the system to make measurements when the probe is placed in an earthed container. The symmetry can improve the measurements by increasing their independence of the position in a container.

The probe can be configured such that the excitation electrodes and a single signal electrode can be configured substantially in parallel, and the signal electrode is positioned between the excitation electrodes in a region between the closest end points of the excitation electrodes. An end point of the signal electrode can be substantially in line with corresponding end points of the excitation electrodes.

The probe can be configured having two excitation electrodes and two signal electrodes arranged substantially in parallel, such that the two signal electrodes are positioned adjacent each other at a position between the excitation electrodes in a region between the closest end points of the excitation electrodes. The end point of the signal electrodes can be substantially in line with corresponding end points of the excitation electrodes. The centre of the signal electrodes can be substantially in line with corresponding end points of the excitation electrodes.

The probe can be configured having two excitation electrodes arranged in parallel, with their ends aligned, and symmetrical about a centre-line of the probe and the two signal electrodes can be arranged substantially in parallel on said centre line equidistant between the excitation electrodes, such that one of the signal electrodes is positioned between the excitation electrodes, in a region between the closest end points of the excitation electrodes, at one end of the excitation electrodes, while the other signal electrodes is positioned between the excitation electrodes, in a region between the closest end points of the other end of the excitation electrodes. The end point of the signal electrodes can be substantially in line with corresponding end points of the excitation electrodes. The centre of the signal electrodes can be substantially in line with corresponding end points of the excitation electrodes. The probe can be configured having two excitation electrodes and four signal electrodes, which are configured substantially in parallel and wherein the four signal electrodes are arranged in couples or pairs adjacent each other at positions between the excitation electrodes, and configured such that (i) a first couple of signal electrodes are arranged between the closest end points of the excitation electrodes at one side of the probe, and (ii) a second couple of signal electrodes are arranged between the closest end points of the excitation electrodes at the other side of the probe. End points of the signal electrodes can be substantially in line with corresponding end points of the excitation electrodes.

The probe can be configured having two excitation electrodes arranged in parallel, with their ends aligned, and symmetrical about a centre-line of the probe and the four signal electrodes, configured substantially in parallel, in couples or pairs, adjacent each other at positions symmetrical about the centre-line and substantially equidistant between the excitation electrodes, such that one pair of the signal electrodes is positioned between the excitation electrodes, in a region between the closest end points of the excitation electrodes, at one end of the excitation electrodes, while the other signal electrode pair is positioned between the excitation electrodes, in a region between the closest end points of the other end of the excitation electrodes. The end point of the signal electrodes can be substantially in line with corresponding end points of the excitation electrodes. The centre of the signal electrodes can be substantially in line with corresponding end points of the excitation electrodes. The probe can be configured having two excitation electrodes arranged substantially in parallel and a single shorter signal electrode is positioned between the excitation electrodes, wherein the excitation electrodes are positioned in a region between the end points of the signal electrode. Corresponding end points of the excitation electrodes can be substantially aligned.

The probe can be configured having two excitation electrodes arranged substantially in parallel and two shorter signal electrodes positioned between the excitation electrodes, wherein the excitation electrodes are positioned in a region between the end points of the signal electrode. Corresponding end points of the excitation electrodes can be substantially aligned. Corresponding end points of the signal electrodes can be substantially aligned.

At least one electrode can be a conductive exposed length of wire material. Additionally or alternatively at least one electrode can be a conductive exposed strip material.

The cross-sectional profile of an electrode can be: substantially circular or elliptical; shallow and substantially rectangular; having a flat base with an arcuate upper section; or a combination thereof.

According to another aspect the invention resides in an apparatus for measuring the biomass content in a medium, the apparatus having a probe as claimed; an output circuit configured to generate an excitation signal for transmission via the probe through a medium, an input circuit configured to receive the excitation signal from the probe after it has passed through a medium; and a means for generating and processing signals.

According to yet another aspect the invention resides in system for performing a fermentation process utilising a culture comprising a suspending liquid and cells, the system having apparatus for measuring the biomass content in a medium, the system having: a probe as claimed; an output circuit configured to generate an excitation signal for transmission via the probe through a medium, an input circuit configured to receive the excitation signal from the probe after it has passed through a medium; a processor and/or electronic circuit for generating and processing signals.

As an overview, the inventor has realised that that the voltage sensing electrodes should be placed (as far as is practical) along a current path which has substantially the same current phase as the total excitation current. The phase of current detected via known probes is an average or weighted average of the phases of all current paths measurable along the length of the or each signal electrode. The embodiments of the invention herein are configured such that voltage sensing electrodes, or signal electrodes, are placed in a position along a current path which has substantially the same current phase as the total excitation current, which is passed in to a medium by the excitation electrodes. In other words the signal electrodes of the invention as claimed are able to measure voltages associated with currents whose phase (or average of the phases) is substantially the same as the current generated by the excitation electrodes. This can be achieved by positioning the signal electrodes in a region of high current density, wherein the influence of the polarisation impedance is minimised or inhibited. This is because a greater proportion of the voltage sensing is in the higher current density region.

By configuring the electrodes of the probe as claimed the relationship between the total excitation current and the measured voltage tends towards the relationship between voltage gradient and the current in the bulk fluid or medium. The impedance calculated, therefore, has substantially reduced error due to the polarisation impedance of the electrode/liquid surface layer and will closely approximate the specific impedance of the fluid.

The specific impedance of simple fluids, e.g. a potassium chloride (KCl) solution can be calculated from first principles, and the inventor has realised that the desired phase of the sensed voltage compared to the measured current is known for such a fluid. This allows the optimum position of the voltage sensing electrodes to be established either empirically or by field modelling. This would preferably be done at the low frequency end of the frequency range where the errors due to the polarisation impedance are most pronounced.

As the voltage sensing electrodes must be of a finite size, they will inevitably disturb the local field to some extent, and will return a voltage which is an approximation of the voltage in that region. However, in practice, it has been found that a dramatic reduction in errors due to electrode polarisation can be achieved by this technique.

The position of the excitation electrodes with respect to the signal electrodes has been described by way of example i.e. with the signal electrodes between the excitation electrodes. In light of the teaching herein a skilled person would recognise that the position of the signal electrodes and the excitation electrodes can be interchangeable.

FIG. 1 illustrates a known probe and has been described above. In order that the invention may be more readily understood, reference will now be made, by way of example, to the drawings in which, FIGS. 2a to 6b are schematic views of an exposed face of a probe according to the invention;

FIGS. 2a to 6b show the exposed face of a probe 10, having an electrically non-conductive base 12 upon which electrodes are mounted. Excitation electrodes 14 are arranged in parallel across the face of the probe 10. One or more signal electrodes 16 are arranged between the excitation electrodes. Alternatively, excitation electrodes can be arranged between the signal electrodes.

Excitation electrodes 14 are alternatively referred to as drive electrodes or current electrodes—they introduce a signal to a medium to be measured. Signal electrodes 16 are alternatively referred to as sensing or voltage electrodes—they are used to measure a voltage therebetween.

The or each signal electrode 16 is substantially parallel to the excitation electrodes. The base 12 is substantially planar such that the electrodes lie on substantially the same plane. The invention (including but not limited to the embodiments of FIGS. 2a to 6b), however, can be implemented with non-parallel electrodes and/or electrodes configured in different planes.

End points A and B are indicated adjacent end points of the excitation electrodes, which are substantially aligned, as viewed, at one side of the probe. End points A' and B' are the end points of the excitation electrodes at the other side of the probe.

An outer end of the or each signal electrode 16 can be substantially aligned with the ends A, B, A', B' of the excitation electrodes.

In use, an excitation signal is passed through a medium between the excitation electrodes 14. The signal electrode(s) 16 are used to detect the potential drop across the medium therebetween. The potential can be detected with a high impedance voltmeter, such that there is virtually no current flowing across the signal electrodes 16 electrode/solution interfaces.

In FIGS. 2a, 3a, 4a, 5a and 6a a three electrode system is shown. The excitation electrodes 14 (the two outer electrodes, as viewed) form a first electrode couple or pair. The signal couple of electrodes 16, for receiving the excitation signal that has passed through the medium, comprise one of the excitation electrodes 14 and a single sensing electrode 16.

In FIGS. 2b, 3b, 4b, 5b and 6b separate couples or pairs of electrodes for excitation and signal detection are provided. To be clear, the signal electrodes 16 comprise first and second electrodes, neither being an excitation electrode.

Figure 4A:
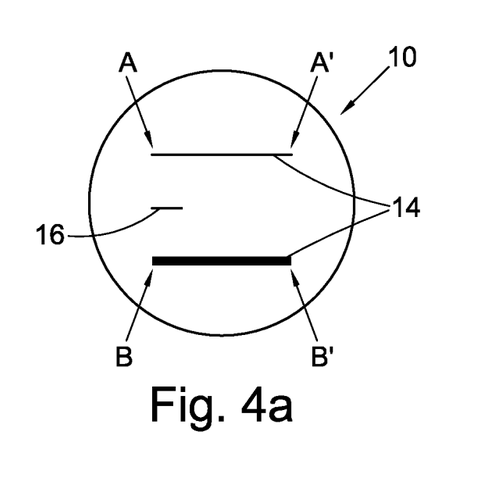
Figure 4B:
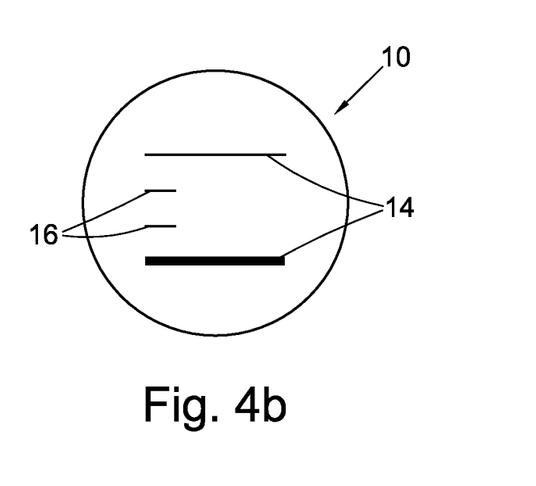
Figure 5A:
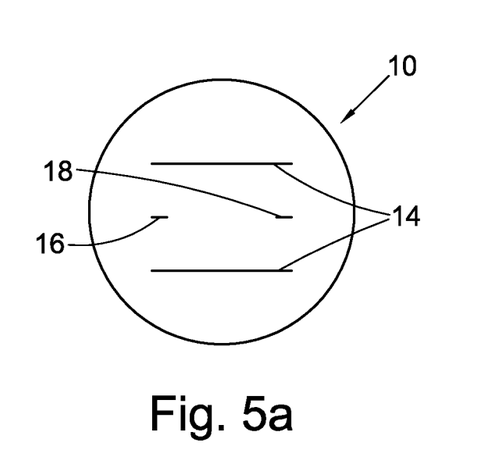
Figure 5B:
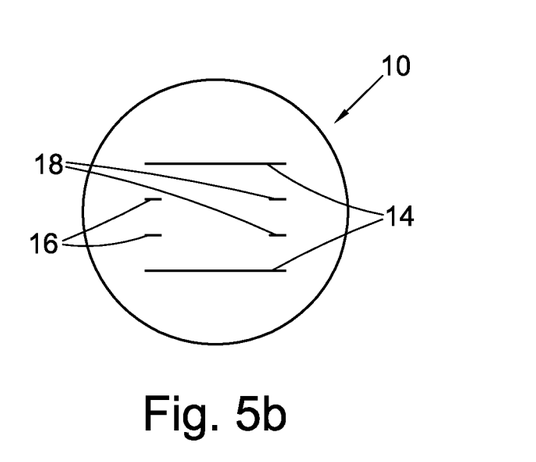

In FIGS. 5a and 5b two signal electrode couples 16 are provided, and represent the preferred configuration of the invention. In this configuration the field generated by the excitation signal is substantially symmetrical such that the potential in a fluid being measured is the same at each end and, therefore, senses the same voltage. In this configuration doubling the surface area of the signal electrodes, with respect to the configuration in FIGS. 4a and 4b, for example, halves the impedance between the electrode and the fluid or medium.

Referring back to FIG. 1, the probe 2 is used to measure a phase difference between the current passed between the outer wires 4 and the voltage measured between the inner wires 6, after having passed through a medium. The inventor has realised that the voltage of the outer wire is the same along its length but the current density varies according to the path the current takes between the wires. The local current density at the end points is higher than in the centre or mid-regions. By taking different paths the phase of the current along different paths will vary because the polarisation impedance (being current dependent) also varies along the excitation electrode's length. Measurement of bulk fluid impedance requires the total electrode current to be measured and a voltage which is a representative weighted mean of that voltage found along all current paths. Because current density is high or higher towards the end of the excitation electrodes the density varies along the length of the excitation electrodes. Known probes (see FIG. 1) provide a spatially averaged voltage which is not representative of that along all the current paths. Further, the phase of the voltage detected by known probes is a weighted average of the voltages on all current paths measurable along the whole length of the or each signal electrode.

Figure 2A:
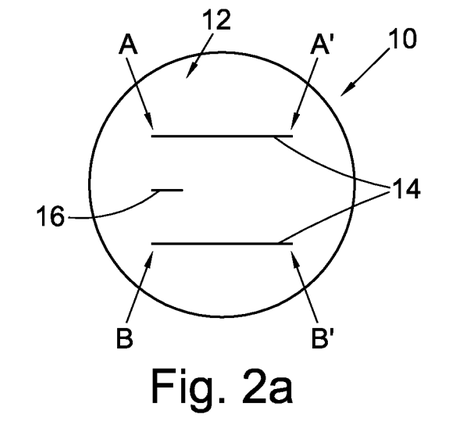

In FIG. 2a, the excitation electrodes 14 are substantially the same length and are arranged to be substantially parallel to each other. The signal electrode is arranged between corresponding end-points of the excitation electrodes 14 i.e. between the closest end-points A and B of the excitation electrodes 14.

Figure 2B:
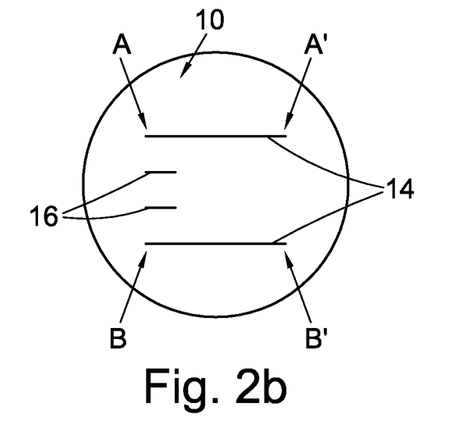

The polarisation impedance depends on current density and with excitation signals up to around 1 MHz the series-equivalent resistance decreases with current density while the capacitance increases. This varying polarisation impedance can introduce errors in the voltage measurements. The current density varies along the length of the excitation electrodes 16. The inventor has realised that the most representative voltage to be measured is proximal, or between, the regions of the end-points A and B, where current density is greatest. The regions of high current density carry the bulk of the total current and consequently errors in the voltage measurement are reduced such that the voltage to be measured is representative of the whole current flow in a medium between the excitation electrodes. In FIG. 2b a signal electrode couple 16 is provided between corresponding end-points of the excitation electrodes 14 i.e. between the closest end-points A and B of the excitation electrodes 14.

Figure 3A:
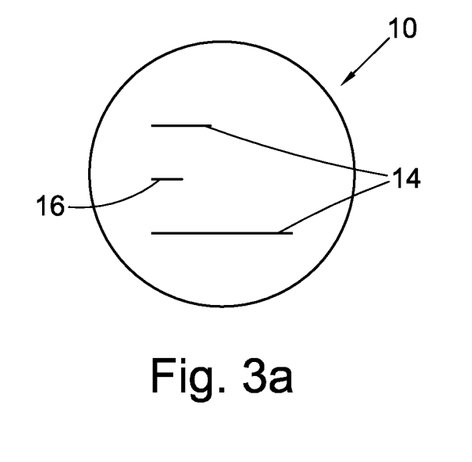

In FIG. 3a, the excitation electrodes 14 are different lengths, but are arranged to be substantially parallel to each other. To be clear, the length A-A' of the uppermost electrode as viewed is shorter than the length B-B' of the lowermost electrode. At one side of the probe 10 the ends of the excitation electrodes A, B are vertically aligned, as viewed. The distance between the corresponding end-points of the excitation electrodes 14 i.e. between the closest end-points A and B of the excitation electrodes 14, is comparable to the probe shown in FIGS. 2a and 2b.

Figure 3B:
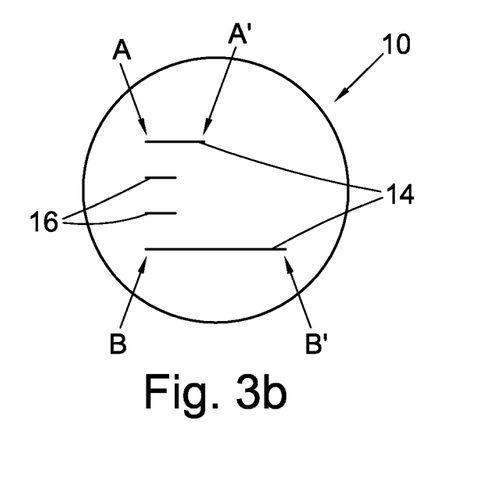

The shorter excitation electrode results in the current density being biased towards the closest end-points A and B. It is in the region of the closest end-points that current density increases, such that there is a lower resistance due to polarisation and the voltage to be measured is more representative of the whole current flow in a medium between the excitation electrodes. In FIG. 3b a signal electrode couple is provided between corresponding end-points of the excitation electrodes 14 i.e. between the closest end-points A and B of the excitation electrodes 14. FIGS. 4a and 4b correspond, respectively, to FIGS. 2a and 2b, but the probes 10 are configured with one of the excitation electrodes 14 (the lowermost electrode, as viewed) having a surface area significantly larger than the other of the excitation electrode couple. The larger surface is at least twice (2×) and preferably at least 5×, and most preferably at least 10× the surface area of the other excitation electrode 14. Said larger electrode can, for example, form a part of the container for the medium being measured. The impedance of the larger electrode (including the contribution due to surface polarisation) is reduced compared to that of the other excitation electrode, and that of the test medium. As a result the voltage will be extremely close to that of the test medium adjacent the large electrode 44.

The probe of FIG. 5a is comparable to the probe of FIG. 2a with an additional signal electrode couple 18. To be clear, a first signal electrode 16 is arranged between corresponding end-points of the excitation electrodes 14 i.e. between the closest end-points A and B of the excitation electrodes 14. A second signal electrode 18 is arranged between corresponding end-points A' and B' of the excitation electrodes 14. In FIG. 5b a first signal electrode couple 16 and a second signal electrode couple 18 are provided between corresponding end-points A and B, and A' and B', respectively i.e. between the closest end-points at each end of the excitation electrodes 14. In FIGS. 5a and 5b the signal electrodes are substantially the same length.

The signal electrodes of FIGS. 5a and 5b are located in the two regions where current density is greatest. By measuring the voltage from the excitation current in the region between each of end-points the signal can be (i) more relevant or stronger, because the signal electrode is provided in two locations thus receiving a voltage, compared to FIGS. 2a and 2b, that has a lower source impedance (twice the contact area with the substance being measured) and/or (ii) more representative of the whole current flow in a medium and/or (iii) the excitation signal is received at two spatially separated positions on the face of the probe 10, for providing a more representative indication of biomass in a medium in which biomass distribution is not evenly distributed.

In FIG. 5a the signal electrodes are connected together. In FIG. 5b the upper-most signal electrodes, as viewed, are connected together, while the lower-most signal electrodes, as viewed, are also connected together but isolated from the upper-most electrodes.

Each signal electrode 16,18 shown in FIGS. 5a and 5b, or any of the other Figures of the invention, can be sensed individually or in groups.

In light of the teaching herein it will be appreciated that the optimum position for a probe configuration can be evaluated. Further, in light of the teaching herein it would appear that the theoretical position of a signal electrode would be right between the very ends of the excitation electrodes.

The inventor has realised through practical tests, however, that positioning the outer ends of the signal electrodes substantially in line with the outer ends of the excitation electrodes can provide improved results. This is illustrated by the embodiments of FIGS. 2a to 5b.

The inventor has also realised through practical tests that the length of the signal electrode influences the results. If the signal electrodes are too short (i.e. below 2 mm in the configuration of FIG. 5b) the polarisation effect is overcompensated. The length of a signal electrode can be less than around one third the length of an excitation electrode i.e. the ratio is 1:3 (e.g. if the excitation electrode was 15 mm long then the signal electrode(s) would be no longer than 5 mm). The ration may be less that 1:4, may be preferably less than 1:5. An optimum ratio can be 1:6.

Figure 6A:
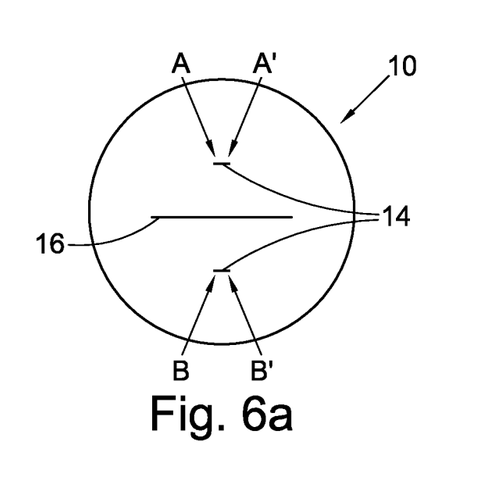
Figure 6B:
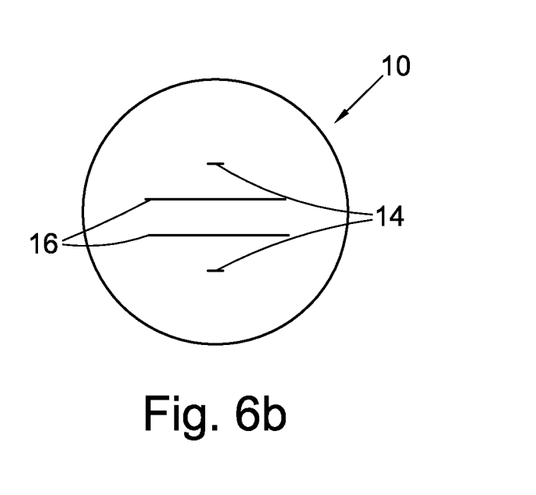

In FIG. 6a, the excitation electrodes 14 are substantially the same length and are arranged to be substantially parallel to each other. The signal electrode 16 is arranged between the excitation electrodes 14 and extend in a parallel direction with respect to the excitation electrodes. In this probe configuration the excitation electrodes are shorter than the signal electrodes and are positioned approximately midway between the end points of signal electrode, as viewed. The current flow between the excitation electrodes 14 is concentrated between points A to B and points A' to B' such that the current density is greater along the path between said points. The current density will vary less along the length of the excitation electrodes 14 and, therefore, the most representative voltage to be measured is proximal, or between, the closest end-points A and B, and A' and B', where current density is greatest. The signal electrode 16 spans a path between points A to B and points A' to B' such that errors in the voltage measurement are reduced because the voltage to be measured is more representative of the whole current flow in a medium between the excitation electrodes. In FIG. 6b a signal electrode couple i.e. two signal electrodes 16 is provided between points A to B and points A' to B' of the excitation electrodes 14.

In FIGS. 4a and 4b one of the electrodes has a greater surface area, which can be implemented using a larger diameter wire or strip, such as an exposed strip material of conductive material. One or more of the aforementioned electrodes 14, 16, 18 can be implemented with such a strip.

The electrodes in FIGS. 2a to 6b are generally formed by an exposed conductive wire. The invention, however, is not so limited and the or each electrode can be formed, by way of example, by: conductive film; deposited conductive material; conductive strips; printed conductive film; conductive strips; or a combination thereof. The shape or footprint of the or each electrode can be configured to optimise the performance in light of the teaching herein. By way of example, the or each electrode can be disc-shaped, having a circular or elliptical footprint, 4-sided footprint or hexagonal footprint.

The shape of the or each electrode can be configured to optimize the contact impedance with a substance in which the probe is immersed. By way of example, minimizing the size of an electrode to lie precisely on a selected current path would result in an increased contact impedance that would detriment performance. In light of the teaching herein a skilled person would be able to optimise the performance.

Further, the cross-sectional profile can, by way of example, be: substantially circular or elliptical, as it would be for a wire; shallow substantially rectangular; having a flat base with an arcuate upper section, such as a hemispherical profile; or a combination thereof.

The electrodes in FIGS. 2a to 6b have been illustrated, by way of example, in a substantially planar configuration. The invention can alternatively be configured in three-dimensional configurations, such as a cylindrical form. The invention can alternatively be configured to increase the length of the current path between excitation electrodes (with respect to those shown in FIGS. 2a to 6b such that the influence of polarisation impedance is minimised.

A number of embodiments have been described above and in order that the performance improvement can be appreciated a comparison will be made between the performance of the probe of FIG. 1 and a representative embodiment of the invention, as shown in FIG. 5b.

The component 2 of FIG. 1 is 25 mm in diameter. All four electrodes are substantially centrally positioned on a flat insulated mount, are 0.5 mm in diameter and have an exposed length of 12 mm. They lie on substantially the same plane. The outer wires 4 are 14.5 mm apart. The inner wires 6 are each positioned 3.5 mm from the outer wires, such that there is 7.5 mm between the inner wires. The outer ends of the electrodes are substantially aligned.

As described above, in order to measure a fluid's specific impedance at a particular frequency it is necessary to measure the voltage across and the current flowing through a representative part of the fluid. The current we can most easily actually measure is the current flowing in the excitation electrodes. This current passes through the metallic electrode, through the metal/liquid interface and into the bulk liquid where it can take many different paths before returning via the other excitation electrode. Although the relationship between the voltage gradient and the current density in the fluid is constant (at a fixed frequency and in a homogeneous liquid) the current density will vary strongly between different current paths. The current density crossing the metal liquid interface layer will also vary significantly over the surface of the electrode (for most electrode configurations, and particularly if the electrodes are to be in one plane). This can be shown using finite element analysis.

The polarisation impedance of this metal liquid interface layer is itself current density dependent, so the layer will introduce series impedance into all the current paths, but this impedance will not be the same for all paths. The currents flowing along the many different paths will therefore not all be in phase with each other. The total excitation current measured will be the sum of all these currents, and will have a phase angle somewhere between the phase extremes of the currents which make it up.

The probe of the invention has one or more signal electrodes, each configured to measure a voltage, which is an average (or weighted average) of the voltages adjacent to it in the fluid, on each current path extending between the excitation electrodes through that region.

In order to measure the impedance of the fluid without interference from the polarisation impedance it is necessary that the phase relationship between the excitation current and the measured voltage is the same as that between the voltage gradient and the current in the bulk fluid.

During a measurement using the probe of FIG. 1 the current paths spread out in 3 dimensions in the adjacent fluid. A consideration of the expected current density distribution on the excitation electrodes suggests that the high and low extremes will be at the ends and centers of the strips. A current path most representative of the total current phase is expected to meet the electrodes away from both of these extreme zones. Using a KCl solution as a test fluid, the impedance and parallel—equivalent capacitance and conductance were calculated from the measured current and voltage using the probe of FIG. 1. For this test solution, the capacitance and the conductance should be frequency independent (within a given frequency range).

Figure 7:
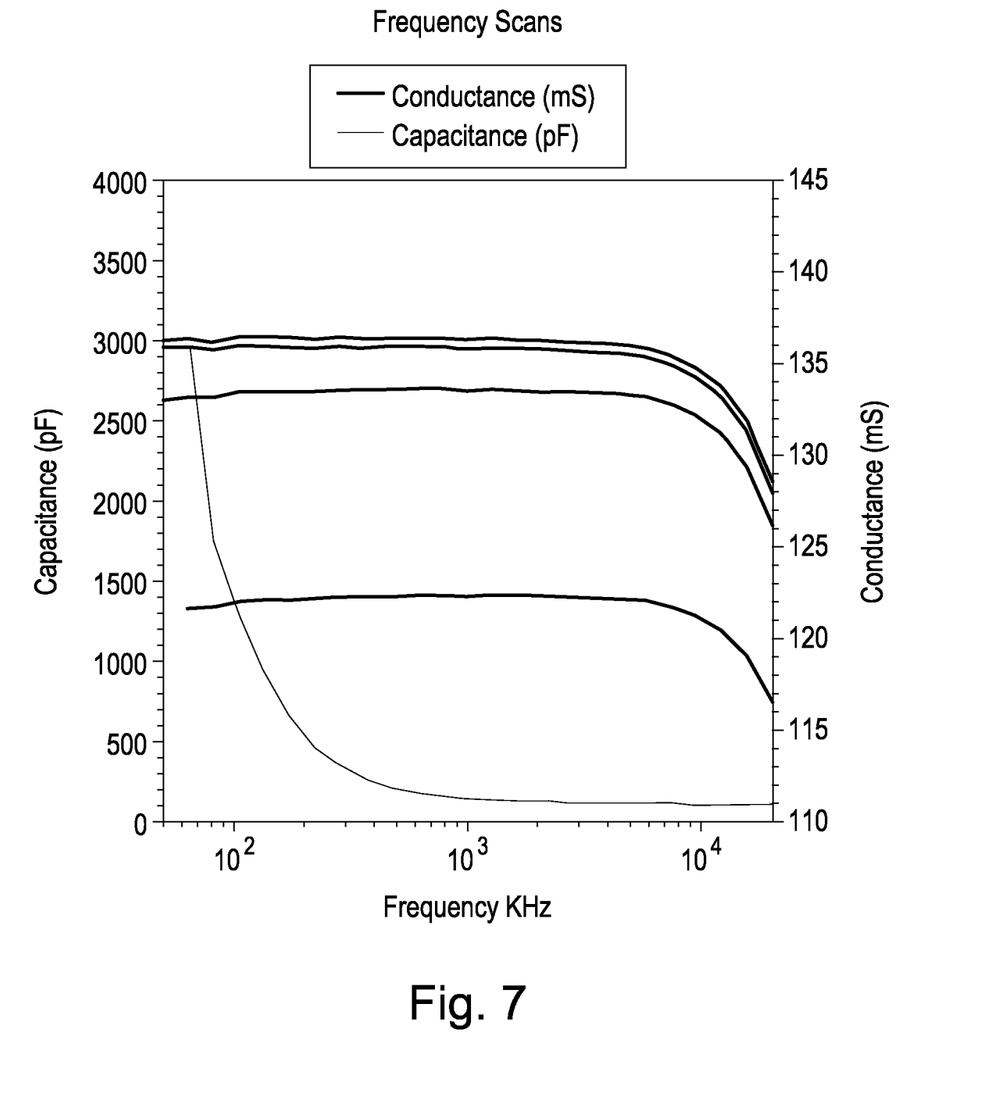
FIG. 7 is a graph showing a frequency scan of a potassium chloride solution using the probe of FIG. 1.

The frequency scan results are shown in FIG. 7. Note the large capacitance error due to electrode polarisation increasing at low frequencies. The configuration of the electrodes in FIG. 1 are such that the errors are large because the voltage electrodes are not sensing the voltage along a representative current path (they will be averaging the voltage over a lot of different paths).

The probe configuration of FIG. 5b was tested. The dimensions of the probe are substantially the same as those in FIG. 1 except that the signal electrodes 16, 18 are shortened with respect to the excitation electrodes 14. Measurements were made with three different variations of the probe shown in FIG. 5b. The length of each signal electrode was the same, but in each variation the signal electrodes were a different length. Three configurations of the probe of FIG. 5b were tested, with each configuration having a different lengths of signal electrode—the configurations tested had signal electrode lengths of 2 mm, 2.5 mm and 3 mm respectively.

For accurate voltage sensing the measuring circuit connected to the sensing electrodes should draw as little current as possible. While this is achievable at low frequencies, measurements at higher frequencies can result in errors in measuring the voltage due to capacitive loading of the electrodes, which exhibit a fairly high source impedance (which increases as electrode area is reduced). This source impedance can be reduced by connecting the sensing electrodes in parallel with an identical pair (or pairs) of electrodes which are sensing an identical voltage—as per the embodiment of FIG. 5b. It is also to be noted that the invention is not limited to connecting sensing electrodes in parallel (as per FIG. 5b) and that the invention provides improvements in performance when only a single electrode couple is used (as per FIG. 5a). In the case of FIG. 5b the field is symmetrical, so a second pair can be placed at the other side of the axis of symmetry.

Figure 8:
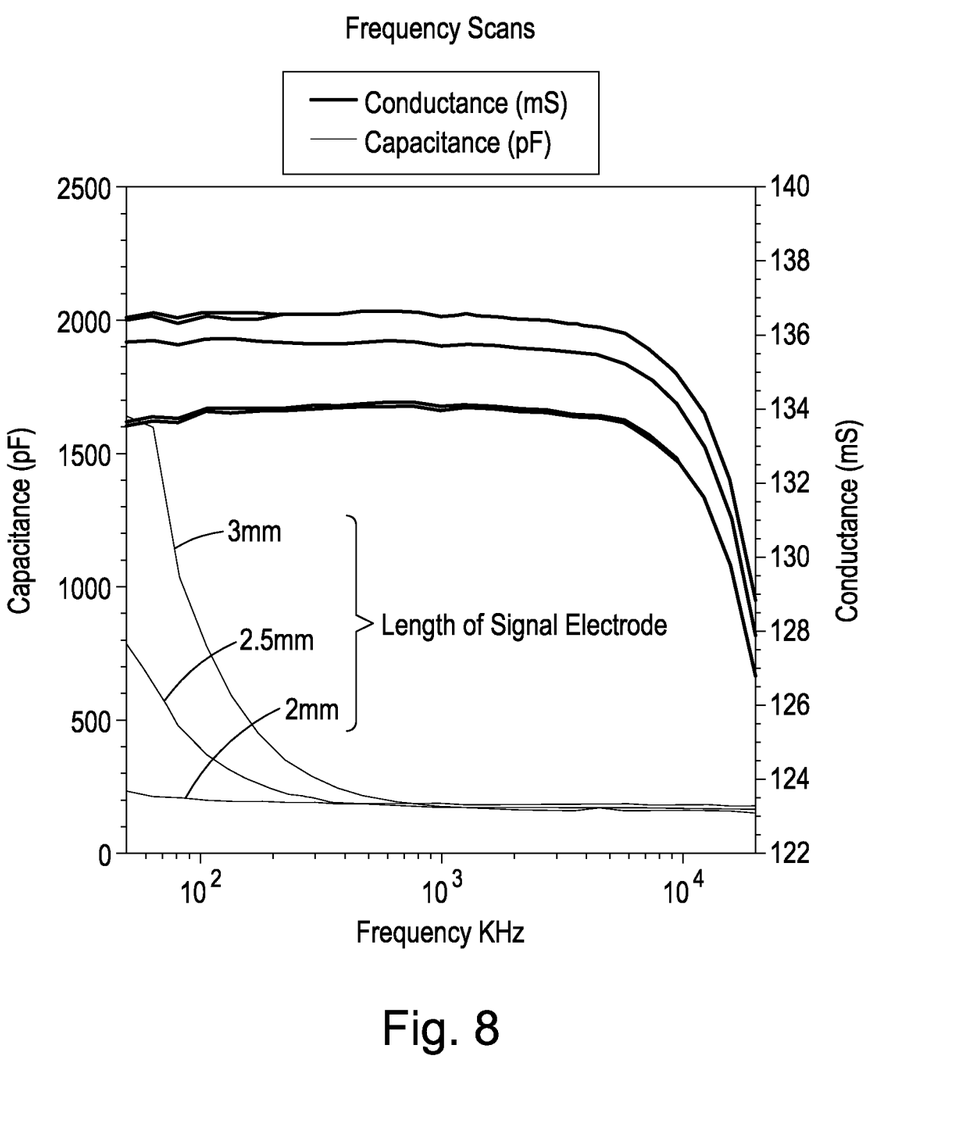
FIG. 8 is a graph showing a frequency scan of a potassium chloride solution using the probe of FIG. 5b.

The frequency scan results using the probe of FIG. 5b is shown in FIG. 8. The capacitance values for each variation (i.e. 3 mm, 2.5 mm and 2 mm probes) are shown and labelled on the left-hand-side of the graph. It can be seen that the capacitance measurement of a probe having the 3 mm long electrodes 16, 18 is almost halved compared to that of the known probe (see FIG. 1). As the length is reduced further the capacitance measurements become more linear across the lower end of the frequency range, such that a probe having sensing electrodes 2 mm in length is able to measure capacitance substantially linearly across the frequency range. The inventor has also realised that in the embodiment of FIG. 5b reducing the length of the sensing electrodes to be less than 2 mm resulted in a lower capacitance reading at low frequencies (sub 1 MHz) resulting in a deviation from a correct value or linear measurement (as viewed). In practice, the error goes the other way and the measurement results using a signal electrode shorter than 2 mm in the given example is such that the measurement would start low, close to the origin, and track upwards before straightening out in a straight-line fashion as the frequency increased. This is because, if too short, over emphasis on the high current flow at the ends becomes unrepresentative of the current passing through the fluid or medium.

Measurements were compared using a known probe (FIG. 1) and an improved probe (FIG. 5b) for illustrative purposes only, and the inventive concept herein can be applied to probes having different configurations such that positioning the sensing electrodes in a position where the current path has substantially the same current phase as the total excitation current. The embodiments of the invention herein are configured such that voltage sensing electrodes, or signal electrodes, are placed in a position along a current path which has substantially the same current phase as the total excitation current, which is passed in to a medium to be measured by the excitation electrodes. The inventor has realised that this can be achieved by the or each signal electrode being located between the two excitation electrodes at a position where high current density occurs i.e. the or each signal electrode is positioned such that the average of the phases of all current paths measurable along the length of the or each signal electrode is substantially the same of the phase of the total excitation current. In the embodiments of the invention herein this occurs in the region between the end of the excitation electrodes. The probe is suitable for use with apparatus for measuring the biomass content in a medium, the apparatus utilising the probe to pass an excitation signal through a medium and subsequently receive the excitation signal from the probe after it has passed through the medium before processing and analyzing the signals.

The probe can be used in a system for performing a fermentation process utilising a culture comprising a suspending liquid and cells, the system having apparatus for measuring the biomass content in a medium, the system utilising the a probe to pass an excitation signal through a medium and subsequently receive the excitation signal from the probe after it has passed through the medium before processing and analyzing the signals.

The subject matter of EP1018025, EP0281602, EP0282532 and GB2481832 is incorporated herein by reference. The present invention has been described above purely by way of example, and modifications can be made within the spirit and scope of the invention, which extends to equivalents of the features described and combinations of one or more features described herein. The invention also consists in any individual features described or implicit herein.

The invention claimed is:

1. A probe for measuring biomass content in a medium having a suspending fluid and cells, the probe comprising:
   at least four electrodes,
   wherein two of the at least four electrodes are configured as excitation electrodes for transmitting an excitation signal through the medium, and said excitation electrodes are configured such that a current density of an excitation signal passing between said excitation electrodes through said medium varies along a length of the excitation electrodes,
   wherein two of the at least four electrodes are configured as signal electrodes for measuring a voltage therebetween that has been generated by an excitation signal passing between the excitation electrodes,
   wherein at least one of the signal electrodes is located between the excitation electrodes at a position where high or higher current density occurs such that the at least one of the signal electrodes is positioned upon, or located on or adjacent, a current path which has substantially a same current phase as a total excitation current,
   wherein the at least one of the signal electrodes is shorter than each of the excitation electrodes.

2. A probe according to claim 1, wherein one of the signal electrodes or each of the signal electrodes is a different length or shape from the excitation electrodes.

3. A probe according to claim 1, wherein a surface area of one of the excitation electrodes is greater than a surface area of another of the excitation electrodes.

4. A probe according to claim 1, wherein a conductive surface area of the excitation electrodes is greater than a surface area of one of the signal electrodes.

5. A probe according to claim 1, wherein one of the signal electrodes or each of the signal electrodes is positioned in a mid-point region between the excitation electrodes.

6. A probe according to claim 1, wherein one of the signal electrodes or each of the signal electrodes is positioned and substantially half-way between the excitation electrodes.

7. A probe according to claim 1, wherein the excitation electrodes are substantially a same length and substantially parallel.

8. A probe according to claim 6, wherein one of the signal electrodes or each of the signal electrodes is configured to be substantially parallel to the excitation electrodes.

9. A probe according to claim 1, wherein the excitation electrodes and one of the signal electrodes are configured substantially in parallel, and the one of the signal electrodes is positioned between the excitation electrodes in a region between closest end points of the excitation electrodes.

10. A probe according to claim 1, wherein the excitation electrodes and two signal electrodes are configured substantially in parallel, wherein the two signal electrodes are positioned adjacent each other at a position between the excitation electrodes in a region between closest end points of the excitation electrodes.

11. A probe according to claim 1, wherein the at least four electrodes comprise an additional two signal electrodes resulting in four signal electrodes, wherein the excitation electrodes and the four signal electrodes are configured substantially in parallel, wherein the four signal electrodes, arranged in couples adjacent each other, at positions between the excitation electrodes, and configured such that (i) a first couple of signal electrodes are arranged between closest end points of the excitation electrodes at one side of the probe, and (ii) a second couple of signal electrodes are arranged between closest end points of the excitation electrodes at an other side of the probe.

12. A probe according to claim 1, wherein at least one electrode of the at least four electrodes is a conductive exposed length of wire material.

13. A probe according to claim 1, wherein at least one electrode of the at least four electrodes is a conductive exposed strip material.

14. A probe according to claim 1, wherein one of the signal electrodes or each of the signal electrodes is less than one third a length of an excitation electrode.

15. A probe according to claim 1, wherein one of the signal electrodes or each of the signal electrodes is less than one fourth a length of an excitation electrode.

16. A probe according to claim 1, wherein one of the signal electrodes or each of the signal electrodes is less than one fifth a length of an excitation electrode.

17. A probe according to claim 1, wherein one of the signal electrodes or each of the signal electrodes is less than one sixth a length of an excitation electrode.

18. An apparatus as recited in claim 1, further comprising:
   an output circuit configured to generate an excitation signal for transmission via the probe through the medium;
   an input circuit configured to receive the excitation signal from the probe after it has passed through the medium; and
   a means for generating and processing signals.

19. An apparatus as recited in claim 1, further comprising:
   an output circuit configured to generate an excitation signal for transmission via the probe through the medium;
   an input circuit configured to receive the excitation signal from the probe after it has passed through the medium;
   a processor and/or electronic circuit configured to generate and process signals.

20. An apparatus as recited in claim 1, wherein each of the excitation electrodes extends between opposing first and second end points, where a distance between a first end point of each excitation electrode is less than a distance between a first end point of one of the excitation electrodes and a second end point of other of the excitation electrodes,
   wherein there is a direct pathway across a separation between the two excitation electrodes,
   wherein the at least one of the signal electrodes is located in a pathway in a region between the respective first end points of the excitation electrodes and not in a region of the pathway between opposing locations intermediate the first and second end points of the respective first and second excitation electrodes.

21. A probe for measuring biomass content in a medium having a suspending fluid and cells, the probe comprising:
- two electrodes configured as excitation electrodes for transmitting an excitation signal through the medium, and said excitation electrodes are configured such that a current density of an excitation signal passing between said excitation electrodes through said medium varies along a length of the excitation electrodes,
- a sensing electrode and one of the excitation electrodes both configured as signal electrodes for measuring a voltage therebetween that has been generated by an excitation signal passing between the excitation electrodes, and
- wherein the sensing electrode is located between the excitation electrodes at a position where high or higher current density occurs such that the sensing electrode is positioned upon, or located on or adjacent, a current path which has substantially a same current phase as a total excitation current,
- wherein the sensing electrode is shorter than each of the excitation electrodes.

* * * * *